US008070733B2

United States Patent
Bettini et al.

(10) Patent No.: US 8,070,733 B2
(45) Date of Patent: Dec. 6, 2011

(54) SEALED DEVICE FOR REGULATING THE FLOW RATE OF MEDICAL LIQUID DIRECTED TOWARDS A PATIENT

(75) Inventors: Emanuele Bettini, Monte San Pietro (IT); Massimo Scagliarini, Casalecchio di Regno (IT)

(73) Assignee: GVS S.p.A., Zola Predosa (IT)

( * ) Notice: Subject to any disclaimer, the term of this patent is extended or adjusted under 35 U.S.C. 154(b) by 81 days.

(21) Appl. No.: 12/299,212

(22) PCT Filed: Apr. 27, 2007

(86) PCT No.: PCT/IB2007/001137
§ 371 (c)(1),
(2), (4) Date: Feb. 11, 2009

(87) PCT Pub. No.: WO2007/125408
PCT Pub. Date: Nov. 8, 2007

(65) Prior Publication Data
US 2009/0192472 A1 Jul. 30, 2009

(30) Foreign Application Priority Data

May 3, 2006 (IT) .............................. MI2006A0864

(51) Int. Cl.
*A61M 5/00* (2006.01)

(52) U.S. Cl. ...................................... 604/248; 604/246

(58) Field of Classification Search .................. 604/248, 604/246, 251, 247, 118, 30, 32; 251/208; 138/43
See application file for complete search history.

(56) References Cited

U.S. PATENT DOCUMENTS

| 2,401,782 | A | | 6/1946 | Weller, Jr. |
| 2,631,811 | A | | 3/1953 | Malloy |
| 2,911,008 | A | | 11/1959 | Du Bois |
| 3,532,127 | A | | 10/1970 | Vogelsang et al. |
| 4,432,387 | A | | 2/1984 | Sims |
| 4,448,212 | A | | 5/1984 | Rubey |
| 4,448,214 | A | | 5/1984 | D'Alessio |
| 5,234,413 | A | * | 8/1993 | Wonder et al. ............... 604/248 |
| 6,364,857 | B1 | | 4/2002 | Gray et al. |
| 2003/0097097 | A1 | * | 5/2003 | Scagliarini et al. .......... 604/246 |
| 2004/0261872 | A1 | | 12/2004 | Mermet |
| 2005/0038387 | A1 | | 2/2005 | Kriesel et al. |

FOREIGN PATENT DOCUMENTS

| EP | 1 312 388 A1 | 5/2003 |
| FR | 2 661 615 A1 | 11/1991 |

* cited by examiner

*Primary Examiner* — Kevin C Sirmons
*Assistant Examiner* — Brandy C Scott
(74) *Attorney, Agent, or Firm* — Novak Druce + Quigg, LLP

(57) ABSTRACT

A device for regulating the flow rate of a medical liquid includes a body provided with elements associated with corresponding parts connected together but torsionally free, at least one of the parts including a plurality of recesses acting as flow regulator able to modify the flow rate of the liquid directed towards the patient by rotating the parts about a common axis of rotation. Between the parts a seal element enables the recesses to be selectively connected together via communication elements, so achieving flow rate regulation. Transverse sealers are provided between the seal element and at least the second part of the parts which are interconnected but torsionally free. The transverse sealers preventing the escape of liquid from the recesses and from the body of the device following a relative movement or misalignment between the parts in a plane perpendicular to the axis of rotation or along this latter during flow regulation or following any angular misalignment of the parts relative to the axis.

15 Claims, 3 Drawing Sheets

SEALED DEVICE FOR REGULATING THE FLOW RATE OF MEDICAL LIQUID DIRECTED TOWARDS A PATIENT

This application is a §371 National Stage Application of International Application No. PCT/IB2007/001137, filed on 27 Apr. 2007, claiming the priority of Italian Patent Application No. MI2006A000864 filed on 3 May 2006.

The present invention relates to a device for regulating the flow rate of a medical liquid to a patient in accordance with the introduction to the main claim.

A device such as the above is the subject of EP1312388 in which it is described as comprising a body provided with elements connected, via suitable conduits, to a reservoir of medical liquid and to a patient. These elements are provided in corresponding parts of said body which are secured together but torsionally free. One of these parts presents, at an end surface facing the other part, a plurality of recesses acting as flow regulator means with which a seal member interposed between said parts cooperates; by means of suitable holes, one through and one dead-ended, this member enables the medical liquid to be transferred from that element connected to the conduit connected to the reservoir, to that element connected to the conduit connected to the patient. This transfer takes place by selectively connecting said recesses together, so as to modify the flow rate of said liquid through the body to the device, said selective connection being achieved by rotating the two parts of said body relative to each other about a common axis of rotation.

Devices equivalent to the aforedescribed, but with different constructional forms, are also described in FR2661615 and U.S. Pat. No. 3,532,127.

Within the device, in particular that of EP1312388 (which represents the state of the art closest to the present invention), the seal member operates to prevent liquid leakages between the first part and the second part of the device body in a direction parallel to the axis of rotation of these parts (coinciding with the longitudinal axis of the body). However it can happen that during flow regulation or during replacement of a conduit connecting said body to the reservoir or to the patient (or rather to the catheter needle inserted into the patient's vein), the person carrying out this operation moves one of the two parts within one of the infinite planes passing through said axis or moves the part along the axis itself. In the first case, the moved part rises on one side away from the other part by pivoting on this latter; in the second case there is total detachment, even though minimum, between the parts. In either case, the seal member is no longer able to properly perform its function, with the result that liquid could leak between the parts to the outside of the device body or inside it.

The problem could be overcome by providing a seal member made of a soft yieldable material (such as natural rubber), but this could influence the ability of this member to correctly connect together the recesses present in a part of the device body and hence could impede correct regulation of the flow of medical liquid towards the patient.

U.S. Pat. No. 5,234,413 describes a device for fluid flow regulation within a medical line. This device comprises two coupled members between which a seal ring is disposed. One of these members presents a dispensing part provided with a groove of variable cross-section connected to a through hole, itself connected to an element for its coupling to a tube for said fluid. The annular seal element presents an aperture allowing communication between said groove and an aperture provided in the other member of the device, and connected to a connector to which another tube of the medical line is connected.

The seal element presents perfectly flat opposing faces and is inserted into a recess provided in only one of said device members. The seal element hence has no projecting rim to provide a correct fluid seal if said members are withdrawn axially from each other or are rotated relative to each other about a fulcrum on their mutual contact region. As the seal element is completely inserted into its seat, any withdrawal or misalignment of said members would enable the fluid present in the groove to escape laterally from the coupling region of said components.

US2004/0261872 describes a flowrate control device in a medical line. This device comprises two components coupled together but free to rotate about a common longitudinal axis; a seal ring or element is present between these components. The seal element, of elastic material, presents a central portion which engages in a recess of a first component and a base resting in a recess of the second component in which a circular groove is provided. The base has a raised peripheral edge which lies between facing portions of the two said components.

This arrangement of the aforesaid US text does not comprise any seat specifically provided for the raised edge of the seal element; consequently, should the two components shift axially or become misaligned (by being raised on one side) during the use of the known device within the medical line in which it is positioned, the fluid passing through them and present in said groove could escape laterally from said components. In this respect, any transverse movement (or lateral raising) of a component would compress the edge of the seal element in the movement direction, whereas it would result in substantial withdrawal of said edge from the moving component at that portion of said edge opposite the compressed portion. This withdrawal would create an escape path for the medical liquid passing through the known device.

U.S. Pat. No. 4,432,387 describes a rotary disc valve for controlling the flow of a fluid in a line along which said fluid moves. The valve comprises a body presenting two facing portions, each comprising a conduit arranged to lie coaxial to the conduit of the other component. These portions house a flow control unit presenting valve seats between which a flow control disc is positioned. The valve laterally comprises means for moving the fluid flow control disc. At opposing ends of this disc, seal elements are present which in one embodiment present opposing edges rising from a flat portion of this element. This known arrangement does not relate to a device for use in a medical line and neither to a device which can present a lateral movement or a relative lifting between its components because of the particular form of the device itself and the presence of the lateral means for moving the central valve element. Again, this known device cannot be subjected to torsion, lifting and movement of its components also because of the presence of fixing elements (screws) distributed perimetrally along the device. The seal elements are located in positions such as to form a seal towards the outside of the device, but any fluid passing through the coaxial conduits could still leak from them and settle between said valve seats and the flow control disc.

Moreover, if this known device were used in a medical line, any residual medical liquid escaping from the coaxial conduits would make the device non longer usable for subsequent liquid infusions for hygienic reasons. In addition, as a medical liquid can also contain sugars, any settling thereof between the components of the device fluid control unit would affect the movement of these components, hence making said device unusable in practice for feeding the correct quantity of medical liquid to a patient.

U.S. Pat. No. 4,448,212 describes a valve for controlling fluid flow for example in a plasmapheresis line. This known valve comprises two mutually facing parts between which a seal element is interposed. On its opposing flat faces, this latter comprises projecting elements (one with a dead hole and two with through holes) to be inserted into boles in the two facing valve components. Again in this case, this known arrangement does not provide correct sealing of the liquid passing through the valve if the valve components become displaced transversely or are raised by their mutual rotation about a contact region. This is because in this case the seal elements present in the holes of said components (defined by conic or cylindrical elements) would tend to undergo compression in the movement direction, but would tend to separate from the wall of the hole in which they are positioned in the opposite direction to the movement. This movement would hence form a recess between the seal elements inserted into the holes and the hole walls, this recess possibly resulting in the leakage of the fluid passing through said valve holes. Hence sealing is efficient only in the movement direction, but not in the opposite direction.

Moreover in the device of this US patent it is also possible for any escaping liquid to collect within an annular portion of one of the two valve components, the seal element partially lying within this annular portion. If the liquid contains sugars, this escape could make it impossible to correctly dispense further fluid or medical liquid passing through a line in which this known valve were to be used following its initial use in a different line. Hence again in this case, problems can arise related to the correct use of the valve in a medical line which derive from possible leakage of the medical liquid within the valve interior, with problems of sugar deposition (which on crystallizing could stick the valve movable parts together), and also related to problems of a hygienic character.

An object of the present invention is to provide a device for regulating the flow rate of medical liquid fed to a patient which represents an improvement over known devices.

A particular object of the invention is to provide a device of the stated type which always provides a proper seal against the liquid traversing it in its transfer from the reservoir to the patient, while enabling correct flow regulation of this liquid.

Another object is to provide a device of the stated type which is of simple construction, while being used in the normal manner.

These and further objects which will be apparent to the expert of the art are attained by a device in accordance with the accompanying claims.

The present invention will be better understood from the accompanying drawings, which are provided by way of non-limiting example and in which.

Figure 1:
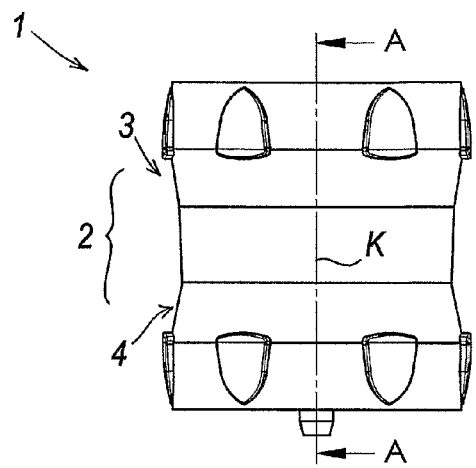
FIG. 1 is a front view of a device according to the invention.

With reference to said figures, a device of the invention is indicated overall by 1; it is essentially similar in its characteristics to the device of EP1312388.

The device 1 comprises a body 2 having a first part 3 and a second part 4, connected together but torsionally free to rotate about an axis of rotation K coinciding with the longitudinal axis of said body 2. The first part 3 comprises a substantially cylindrical connection element 6 with an internal conduit 6A enabling the part 3 to be connected to a first conduit (not shown) of a medical infusion line and through it to a bag or reservoir of medical liquid. The second part 4 comprises a substantially cylindrical connection element 8 with an internal conduit 8A to which a second conduit (not shown) is connected carrying this liquid to a patient.

Between the first part 3 and the second part 4 an annular seal element 10 is positioned disposed between faces 11A and 12A of flat end portions 11 and 12 of said parts 3 and 4, and at least partially inserted into a seat 11K of the face 11A. From the face 11A of the flat portion 11 of the part 3 a connection element 13 projects in known manner, disposed along said longitudinal axis K and cooperating with a hollow counter-connection element 14 of the second part to axially connect these parts together, while enabling them to rotate relatively about the axis K. The counter-connection element 14, of known type, projects from a face 12B of the flat portion 12, from said face there also projecting the said connection element 8; the counter-element 14 is preferably obtained from a plurality of walls 16 disposed to define a cylindrical seat (the counter-element 14) for receiving the connection element 13.

Each part 3 and 4 is essentially of cup shape. The part 3 has a perimetral wall 20 rising from the edge of the flat portion 11, while the second part 4 has a perimetral wall 21 rising from the edge of the flat portion 12.

At least the part 4 comprises on the face 12A of the flat end portion 12 at least one and preferably a plurality of recesses 25 (of variable depth and/or width, i.e. of variable size) connected to the connection element 8 and acting as communication means to transfer the medical liquid from the conduit connected to the bag or reservoir to the conduit connected to the patient, said liquid passing through the connection elements 6 and 8. A face 28 of the seal element 10 is disposed above said recesses 25, a dead-ended hole 30 being provided in said face. Finally the seal element 10 comprises, in the manner known from EP1312388, a through hole 31 connected directly to the conduit 6A of the connection element 6 and receiving therefrom the medical liquid originating from the bag to which said element is connected by the corresponding conduit.

The seal element 10 acts as a seal member to prevent leakage of medical liquid in directions parallel to the longitudinal axis K of the body 2.

According to the invention, transverse sealing means for the fluid are provided between said seal element 10 and at least one of the parts 3 and 4 of the body 2, these sealing means preventing liquid leakage from the body 2 when said parts are spaced apart along the axis K or are moved relative to each other in a plane perpendicular thereto, said movement involving the local raising of one part relative to the other at the edge of the flat portions 11 and 12.

Figure 2:
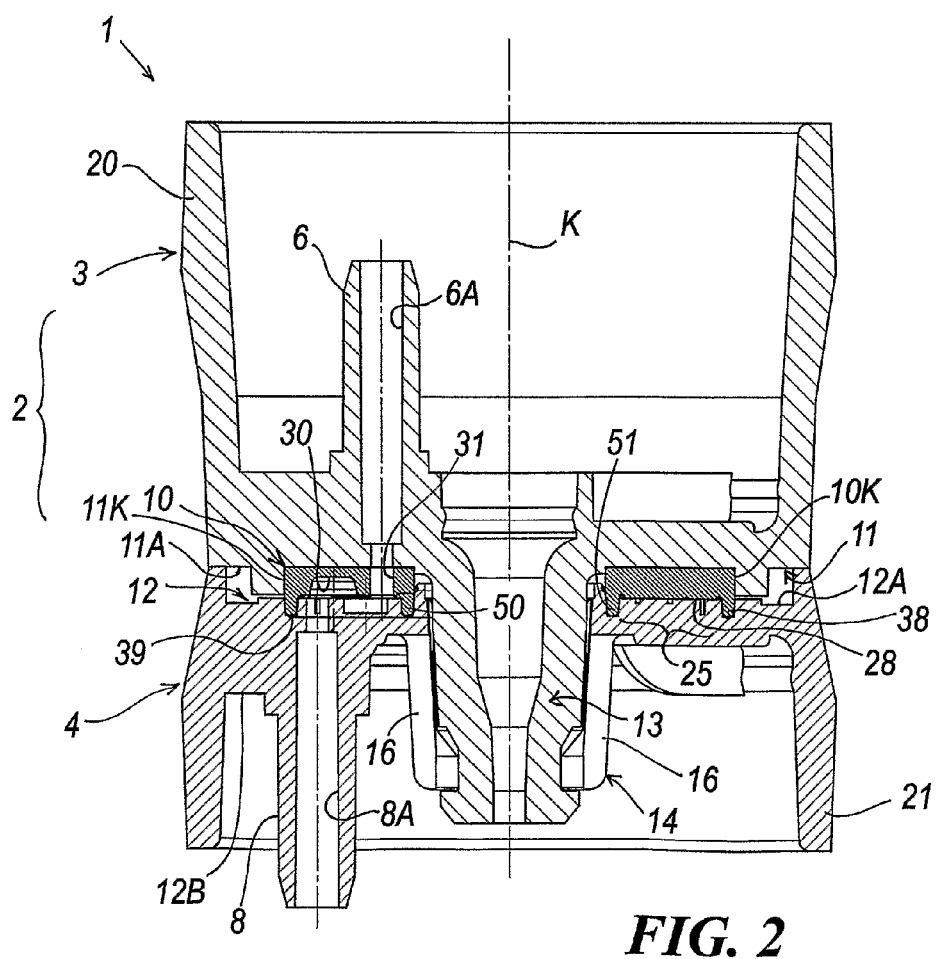
FIG. 2 is a cross-section through a first embodiment of the device of FIG. 1.

More specifically, FIG. 2 shows a first embodiment of the invention in which the seal element presents a preferably continuous (but alternatively discrete) first annular rim 38 extending from that face 28 of the seal element 10 facing the face 12A of the portion 12 of the second part 4 of the body 2. This continuous annular rim 38 is external (with reference to the axis K) to each recess 25 (which is hence positioned between the rim and the axis K) and penetrates, preferably but not necessarily as a form fit, into an annular recess 39 specifically provided in said face 12A such that even slight lifting of the part 3 relative to the part 4 or limited axial detachment between these parts does not necessarily result in exit of the annular rim 38 from the recess 39. As stated, this rim and recess are disposed external to the recesses 25 provided in the face 12A of the portion 12, i.e. external to the most outer recess provided in this face (with reference to the longitudinal axis K and starting therefrom) and hence prevent transverse leakage (towards the outside of the device) of the liquid contained in these recesses when total or partial but in any event always limited detachment between the parts 3 and 4 of the body 2 occurs. The term "transverse leakage" of the fluid means fluid leakage in a direction transverse to the axis or at the portions 11 and 12 of the parts 3 and 4 of the body 2 of the device 1, i.e. where the body 2 comprises a discontinuity arising from the engagement between these parts. According to the invention, the annular element 10 presents a second continuous annular raised edge 50 at the most inner recess (i.e. closest to the longitudinal axis or axis of rotation K) of the face 12A of the portion 12 of the second part 4. This second rim 50 cooperates with a corresponding annular recess 51 provided in the face 12A of said portion 12; in this recess, the rim 50 is preferably disposed as a form fit with the rim 38 in the recess 39.

The arrangement enables an excellent fluid seal to be obtained both at the most inner part, close to the axis K, of the flat portion 12 of said part 4, and at the most outer part of that portion.

As the rims 38 and 50 are inserted into seats (39 and 51) provided in both the parts 3 and 4 of the body 2, the fluid seal is achieved optimally whatever the relative movement present between said parts 3 and 4. The seal is complete about the recesses 25 (or otherwise about a single recess which may be present in the face 12A of the portion 12).

Figure 3:
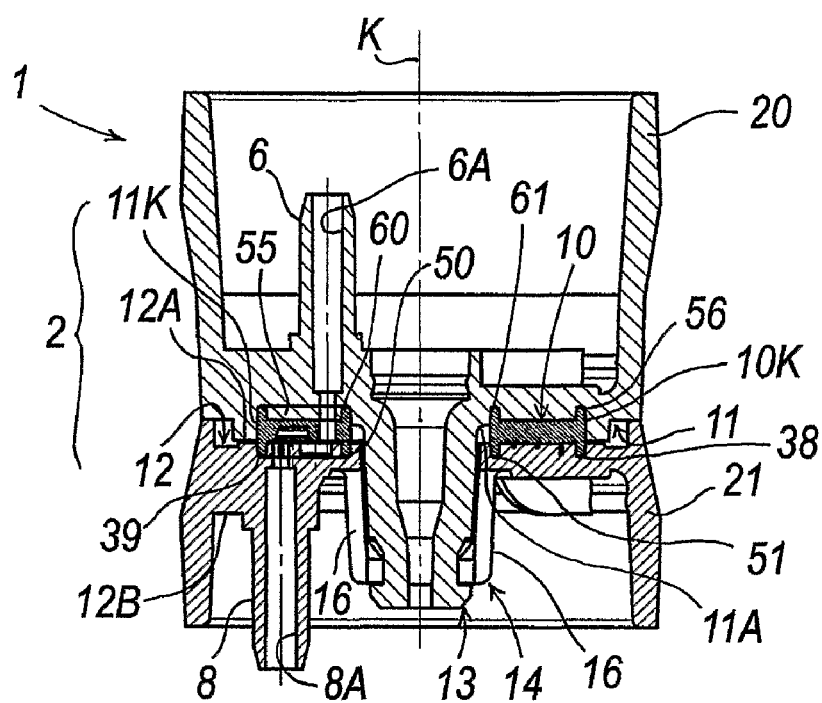
FIG. 3 is a view similar to that of FIG. 2, but of a second embodiment of the invention.
Figure 4:
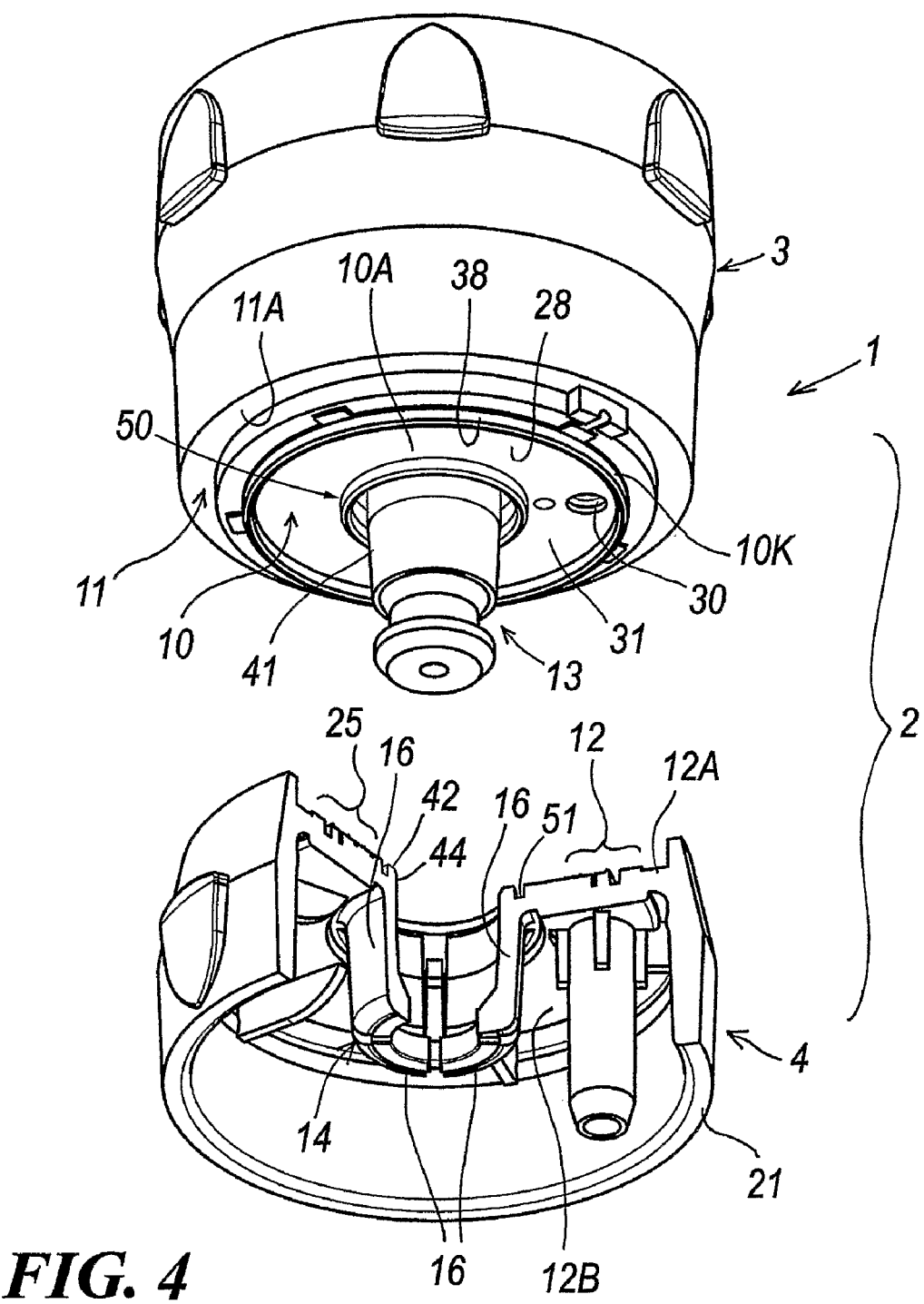
FIG. 4 is a partly sectional and partly exploded perspective view of the device of FIG. 1, in the embodiment of FIG. 2.

A variant of the invention is shown in FIG. 3 in which parts corresponding to those already described are indicated by the same reference numerals. In this figure, the seal element 10 comprises a pair of concentric spaced-apart annular rims provided both on that face 28 facing the face 12A of the portion 12 of the part 4 and on that face 55 facing the face 11A of the portion 11 of the part 3. In other words, at the inner edge of the annular element 10 close to the central hole 42 there are provided two rims 50 and 60 facing in opposite directions and cooperating, preferably as a form fit, with respective recesses 51 and 61, said rims providing a liquid seal in proximity to the axis K; likewise, in proximity to the side 10K other opposing rims 38 and 56 are provided facing the parts 3 and 4 of the body 2. The pairs of annular rims provided on the opposing faces of the seal element 10 embrace both the recesses provided in the face 12A of the portion 12 of the second part 4 and the inner conduit 6A of the connection element 6 provided in the interior of the first part 3 of the body 2 and opening into the face 11A of the portion 11 of this latter within the pair of rims present on the face 55 of the element 10. By virtue of the invention an excellent seal, both axial and transverse, is obtained for the device for regulating the flow rate of a medical liquid directed towards a patient. This seal is provided both towards the outside of the body and towards the axis of this latter.

Various embodiments of the invention have been described in which the element 10 comprises one or more rims cooperating with corresponding recesses in at least one of the parts 3, 4 of the body 2 of the device. The present document also comprises any dual arrangement, i.e. in which at least one of the parts 3 and 4 comprises a rim projecting towards the element 10, which comprises a corresponding recess for receiving it. These variants and others obtainable by the expert of the art on the basis of the present document are to be considered as falling within the scope of the accompanying claims.

The invention claimed is:

1. A device for regulating the flow rate of a medical liquid directed towards a patient, comprising:
    a seal element presenting a continuous annular first recess;
    a body provided with elements connected to conduits for connecting respectively to a reservoir of said liquid and to the patient, said elements associated with corresponding parts connected together but torsionally free, said corresponding parts comprising at least a first part and a second part,
    at least the second part comprising at least one second recess of variable size for regulating flow to modify the flow rate of said liquid directed towards the patient by rotating said parts about a common axis of rotation,
    the second part provided with the second recess comprising an aperture in its flat portion, through said aperture there passing a connection element for the first part, to cooperate with a counter-element on said second part provided with the second recess,
    between said first and second parts there being said seal element which enables fluid to pass, via communication means, from the first part of the device body to the second part of the device body via said at least one second recess for said flow rate regulation,
    transverse liquid sealing means between said seal element and at least the second part, provided with the at least one second recess, of said interconnected parts,
    said transverse sealing means for preventing the escape of liquid from said second recess and from the body of the device following a relative movement between said first and second parts in a plane perpendicular to said axis of rotation or along this axis during flow regulation or following any angular misalignment of said first and second parts relative to said axis,
    said transverse seal means comprising a continuous first rim rising from said seal element, said first rim being more external than the second recess with reference to the axis of rotation which coincides with the longitudinal axis of said body, the second part of the body provided with the second recess presenting the continuous first recess to receive the projecting continuous first rim,
    wherein the seal element is a single one sealing element; and
    said transverse seal means comprises a second annular rim projecting from said seal element,
    said second rim being disposed more internal than the second recess of said second part with reference to the longitudinal axis of the device body,
    said second annular rim and the more external first rim embracing each recess provided in the face of the flat portion of said second part, wherein said second rim cooperates with a corresponding third recess provided in said second part provided with the second recess, said second rim and the corresponding third recess being so provided to obtain a fluid seal close to the above-cited axis of rotation, each projecting rim cooperating substantially as a form fit to seat with the corresponding recess.

2. A device as claimed in claim 1, wherein each projecting rim is a full body.

3. A device as claimed in claim 1, wherein the first rim is a first annular rim, and said projecting annular rims are provided in that face of the seal element facing the face of a flat portion of that second part provided with said at least one second recess in which said second recess is provided, in said face of said flat portion there being provided the recesses for said projecting rims.

4. A device as claimed in claim 1, wherein the second part of the device body comprises a plurality of recesses to be selectively connected by said communication means of the seal element, said recesses being embraced by said outer first rim and by said second annular rim.

5. A device as claimed in claim 1, wherein in proximity to the aperture of the second part provided with a recess the second part presents a collar rising from the face of the flat portion in which said recesses are provided, with said collar there cooperating the second annular rim of the seal element on the inside of the central hole of this latter.

6. A device as claimed in claim 1, comprising a further third annular rim positioned between the seal element and that first part of the device body provided with the element for connection to the medical liquid reservoir, said further rim rising from a flat face of one from among said element and said second part, said further third rim cooperating with a seat provided in the other from among said seal element and said first part of the body.

7. A device as claimed in claim 6, wherein the further third rim is provided in a side of the seal element.

8. A device as claimed in claim 6, wherein a seal collar is provided between the seal element and that second part provided with recess, to form between said element and the part a seal substantially perpendicular to the longitudinal axis of the device.

9. A device as claimed in claim 8, wherein the seal collar projects from the side of the seal element.

10. A device as claimed in claim 6, wherein the further third rim rises from that face of the seal element facing the first part of the body, in this first part of the body there being provided the seat for said rim.

11. A device as claimed in claim 1, further comprising third and fourth annular rims, wherein said first, second, third and fourth rims are arranged as pairs of concentric continuous annular rims associated with one from among said seal element, said first part of said device body and said second part of the device body, said pairs embracing the recesses provided in the second of said parts and an aperture for the connection element in the flat portion of the first part of said body.

12. A device as claimed in claim 11, wherein each annular rim cooperates with a corresponding continuous recess provided in the other from among said connection element, the first part of the device body and the second part of the device body.

13. A device as claimed in claim 11, wherein the pairs of annular rims project from those opposing faces of the seal element facing the corresponding parts of the device body, the rims of said pairs being spaced apart and embracing, on the respective faces, the recesses of the second part and the aperture of an inner conduit of the connection element of the first part, said first and second parts having corresponding recesses for these rims.

14. A device as claimed in claim 1, wherein said seal element is an annular seal element, and said continuous first rim is a continuous annular first rim.

15. A device as claimed in claim 1, wherein said third recess has a U-shaped annular cross-section.

* * * * *